US006971382B1

(12) United States Patent
Corso

(10) Patent No.: US 6,971,382 B1
(45) Date of Patent: Dec. 6, 2005

(54) TRACHEA TUBE METHOD AND DEVICE

(76) Inventor: Albert M Corso, 175 Randall Rd., Shorham, NY (US) 11786

( * ) Notice: Subject to any disclaimer, the term of this patent is extended or adjusted under 35 U.S.C. 154(b) by 0 days.

(21) Appl. No.: 10/852,623

(22) Filed: May 24, 2004

(51) Int. Cl.⁷ .......................................... A61M 16/00
(52) U.S. Cl. ......................... 128/200.26; 128/207.15; 128/207.29
(58) Field of Search .................... 128/200.26, 207.15, 128/207.16, 207.29, 912; 623/9

(56) References Cited

U.S. PATENT DOCUMENTS

| | | | | |
|---|---|---|---|---|
| 3,137,299 A * | 6/1964 | Tabor .................... | 128/207.16 |
| 3,263,684 A * | 8/1966 | Bolton ................... | 128/207.16 |
| 3,659,612 A * | 5/1972 | Shiley et al. .......... | 128/207.15 |
| 3,889,688 A * | 6/1975 | Eamkaow .............. | 128/207.15 |
| 4,246,897 A * | 1/1981 | Muto ..................... | 128/207.15 |
| 4,274,162 A * | 6/1981 | Joy et al. ............... | 623/9 |
| 4,280,492 A * | 7/1981 | Latham .................. | 128/207.15 |
| 4,340,046 A * | 7/1982 | Cox ....................... | 128/207.17 |
| 4,364,391 A * | 12/1982 | Toye ..................... | 128/207.29 |
| 4,435,853 A * | 3/1984 | Blom et al. ............ | 623/9 |
| 4,449,523 A * | 5/1984 | Szachowicz et al. ... | 128/200.26 |
| 4,459,984 A * | 7/1984 | Liegner ................. | 128/207.15 |
| 4,471,778 A * | 9/1984 | Toye ..................... | 128/207.29 |
| 4,596,248 A * | 6/1986 | Lieberman ............. | 128/207.16 |
| 4,808,183 A * | 2/1989 | Panje .................... | 623/9 |
| 4,852,565 A * | 8/1989 | Eisele ................... | 128/207.14 |
| 4,877,025 A * | 10/1989 | Hanson ................. | 128/204.16 |
| 5,048,518 A * | 9/1991 | Eliachar et al. ........ | 128/207.14 |
| 5,054,484 A * | 10/1991 | Hebeler, Jr. ........... | 128/207.16 |
| 5,056,515 A * | 10/1991 | Abel ..................... | 128/207.15 |
| 5,064,433 A * | 11/1991 | Blom et al. ............ | 623/9 |
| 5,217,005 A * | 6/1993 | Weinstein ............. | 128/200.26 |
| 5,217,008 A * | 6/1993 | Lindholm ............. | 128/207.14 |
| 5,339,809 A * | 8/1994 | Beck et al. ............ | 128/207.29 |
| 5,653,230 A * | 8/1997 | Ciaglia et al. ......... | 128/207.15 |
| 5,957,978 A * | 9/1999 | Blom .................... | 623/9 |
| 6,053,167 A * | 4/2000 | Waldeck ................ | 128/207.14 |
| 6,135,110 A * | 10/2000 | Roy ...................... | 128/207.15 |
| 6,612,305 B2 * | 9/2003 | Fauza .................... | 128/200.26 |

* cited by examiner

Primary Examiner—Aaron J. Lewis
(74) Attorney, Agent, or Firm—Michael I. Kroll

(57) ABSTRACT

Method and apparatus for a trachea tube 12 having an interiorly positioned retaining member 14 and a flange 16 forming an exteriorly positioned retaining member. The trachea tube 12 has means 14, 16 that permits the tube to be held firmly in the proper position upon a person on whom the device is installed. The tube 12 maintains the stoma open in case the person moves the trachea tube 12. The tube 12, when inserted and capped into the trachea 20, allows air flow 22 through the normal anatomical passageway and allows the person to speak and swallow food easier.

14 Claims, 8 Drawing Sheets

STEP 1

STEP 2

STEP 3

STEP 4

STEP 5

TRACHEA TUBE METHOD AND DEVICE

BACKGROUND OF THE INVENTION

1. Field of the Invention

The present invention relates generally to tracheotomy tubes and, more specifically, to a method and apparatus for a trachea tube having an interiorly positioned retaining member and a flange forming an exteriorly positioned retaining member. Said trachea tube having means that permits the tube to be held firmly in proper position upon a person on whom the device is installed. The tube maintains the stoma open. The tube, when inserted and capped into the trachea allows gas flow through the normal anatomical passage ways, allows person to speak and allows person to swallow food easier. The tube allows easy access for suctioning the patient.

2. Description of the Prior Art

There are other trachea tubes designed for the same means. Typical of these is U.S. Pat. No. 507,813 issued to Hartstein on 31, Oct. 1893.

Another patent was issued to Brehm on Apr. 28, 1936 as U.S. Pat. No. 2,039,142. Yet another U.S. Pat. No. 2,765,792 was issued to Nichols on Oct. 9, 1956 and still yet another was issued on Mar. 26, 1957 to Cohen as U.S. Pat. No. 2,786,469.

Another patent was issued to Giraudon on Aug. 27, 1957 as U.S. Pat. No. 2,804,076. Yet another U.S. Pat. No. 3,088,466 was issued to Nichols on May 7, 1963. Another was issued to Tabor on Jun. 16, 1964 as U.S. Pat. No. 3,137,299 and still yet another was issued on Aug. 8, 1967 to Stebleton U.S. Pat. No. 3,334,631.

Another patent was issued to Birch, et al. on Aug. 6, 1974 as U.S. Pat. No. 3,827,440. Yet another U.S. Pat. No. 3,973,569 was issued to Sheridan on Aug. 10, 1976. Another was issued to La Rosa on Jul. 5, 1977 as U.S. Pat. No. 4,033,353 and still yet another was issued on Nov. 16, 1999 to Turner as U.S. Pat. No. 5,983,895. Another was issued to Nash on Aug. 3, 2000 as U.K. Patent No. GB 2,341,102.

A cannula comprising two tubes fitting one within the other, the outer one being capable of an outward movement independently of the inner tube, and means, located at the outer ends of the tubes for holding the latter in position, substantially as described.

In combination, a necklace and a tracheotomy tube, said necklace including a member secured to and constituting a screen upon the otherwise exposed end of said tracheotomy tube.

A tracheal device comprising an outer tube adapted to be inserted into the trachea of a user, and an inner tube freely insertable into said outer tube through one end thereof, at least one of said tubes being made of a resilient material, said outer tube having a reduced internal diameter at its opposite end of such dimension as to frictionally receive and grip said inner tube as the corresponding end thereof by reason of the resilience of said one tube whereby to releasably hold said tubes in mated relation.

A translucent tracheal tube assembly which includes an outer cannula, an inner cannula and flange.

A surgical device intended for patients having undergone the operation of laryngotomy.

A tracheal device comprising an outer tube adapted to be inserted into the trachea of a user and having an entrance for reception of an inner tube therein and an inner tube insertable into said outer tube through said entrance end thereof to be mated therewith, said inner tube having a corresponding entrance end and a radial enlargement adjacent thereto adapted to frictionally engage the inside surface of said outer tube when said tubes are in mated relation to thereby releasably hold said tubes in said mated relation.

A tracheotomy tube comprising an annular wall defining a duct, said tube being formed of a synthetic resin and being integrally provided at one end with an annular resilient flange having a sufficient degree of flexure so as to be easily insertible through the artificial passage surgically formed in the patients neck, said flange being connected endwise to the duct by an annularly reduced resilient constriction which is thinner than the wall-thickness of the duct and is thereby readily and easily deformed to permit insertion and when so inserted, will spring back so that the flange will be in seated engagement against the internal surface of the patient's tracheal wall, said annular wall being of sufficient length to extend through and project beyond the exterior of the patient's neck, and valve means operatively mounted across said projecting end.

A tracheal device comprising a flexible outer tube having predetermined curvature and adapted to be inserted into the trachea of the user through an incision in the throat, and flexible inner tube having an external diameter slightly smaller than the internal diameter of the outer tube and being freely insertable into the outer tube.

A removable check-valve for installation on the external portion of a tracheotomy tube including a housing containing a free-floating, flat type disc for opening and closing the tracheotomy tube during the breathing cycle regardless of the body position of the user. An auxiliary port may be provided on the housing for supplying supplemental oxygen continuously to the user direct loss of oxygen to the atmosphere.

Tracheostomy tubes are provided with means that permits them to be held firmly in proper position upon a person on whom the device is installed. Such means comprises a fixed flange member, a slideable flange member and a plurality of slideable and separately removeable ring members positioned between the fixed and slideable flange members.

A tracheostomy tube, shaped to conform to the trachea, and including an inner and an outer cannula. The extremities of the cannulae inserted in the trachea are in frictional contact to prevent significant gas flow through the annular space between the cannulae. The opposite extremity of the outer cannula is shaped for connection to a respirator with the corresponding end of the inner cannula attached to an adaptive member through a nutating connection. The adaptive member is shaped at its inner end for connection to the outer cannula and at its outer end to a respirator. The outer cannula may include an inflatable cuff for sealing the cannulae within the trachea and a flexible neck flange for limiting the motion of the tracheostomy tube.

A tracheostomy tube assembly comprises an outer tracheostomy tube and an inner cannula of a flexible material preformed to the shape of the outer tube and smooth on its inside and outside. The outer tube is straight at its patient end and has a short straight machine end with a coupling. The patient and machine ends are separated by a curved intermediate region divided along its length into two sub-regions. The first sub-region closer the machine end has a small radius of curvature; the other sub-region closer to the patient end has a radius of curvature at least three times that of the first sub-region. This shape enables the patient end of the assembly to be aligned with the patient's trachea.

An introducer for a medical tube, the introducer having a patient end nose a part of which is arranged to protrude from a patient end of tube, and the nose having a passage therethrough for receiving a guide wire, wherein the passage opens at the patient end of the nose through an aperture that lies on a plane extending at right angles to the passage and inclined away from the normal to the axis of the nose.

While these trachea tube devices may be suitable for the purposes for which they were designed, they would not be as suitable for the purposes of the present invention, as hereinafter described. The present invention, a trachea tube having an interiorly positioned retaining member and a flange forming an exteriorly positioned retaining member. Said trachea tube having means that permits said tube to be held firmly in proper position upon a person on whom the device is installed. The tube maintains the stoma open. The tube, when inserted into the trachea and capped allows gas flow through the normal anatomical passage ways, allows a person to speak easier, cough up secretions easier and to swallow food and drink easier. The tube allows easy access for suctioning the patient.

SUMMARY OF THE PRESENT INVENTION

The present invention discloses a method and apparatus for a trachea tube having an interiorly positioned retaining member and a flange forming an exteriorly positioned retaining member. The trachea tube has means that permits the tube to be held firmly in the proper position upon a person on whom the device is installed. The tube maintains the stoma open. The tube, when inserted and capped into the trachea, allows air flow through the normal anatomical passageway and allows the person to speak, cough and swallow food easier. The tube allows easy access for suctioning the patient.

A primary object of the present invention is to provide a trachea tube having an inflatable interiorly positioned retaining member.

Another object of the present invention is to provide a trachea tube having a flange forming an exteriorly positioned retaining member.

Yet another object of the present invention is to provide a trachea tube having means that permits said tube to be held firmly in proper position upon a person on whom the device is installed.

Still yet another object of the present invention is to provide a trachea tube that when inserted into the trachea and capped maintains contact with the trachea to allow significant gas flow through the normal anatomical passage ways.

Additional objects of the present invention will appear as the description proceeds.

The present invention overcomes the shortcomings of the prior art by providing a trachea tube having an interiorly positioned retaining member and a flange forming an exteriorly positioned retaining member. Said trachea tube having means that permits said tube to be held firmly in proper position upon a person on whom the device is installed. The tube maintains the stoma open. The tube, when inserted into the trachea and capped allows gas flow through the normal anatomical passage ways, allows a person to speak easier, cough up secretions easier and to swallow food and drink easier.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

LIST OF REFERENCE NUMERALS

Figure 1:
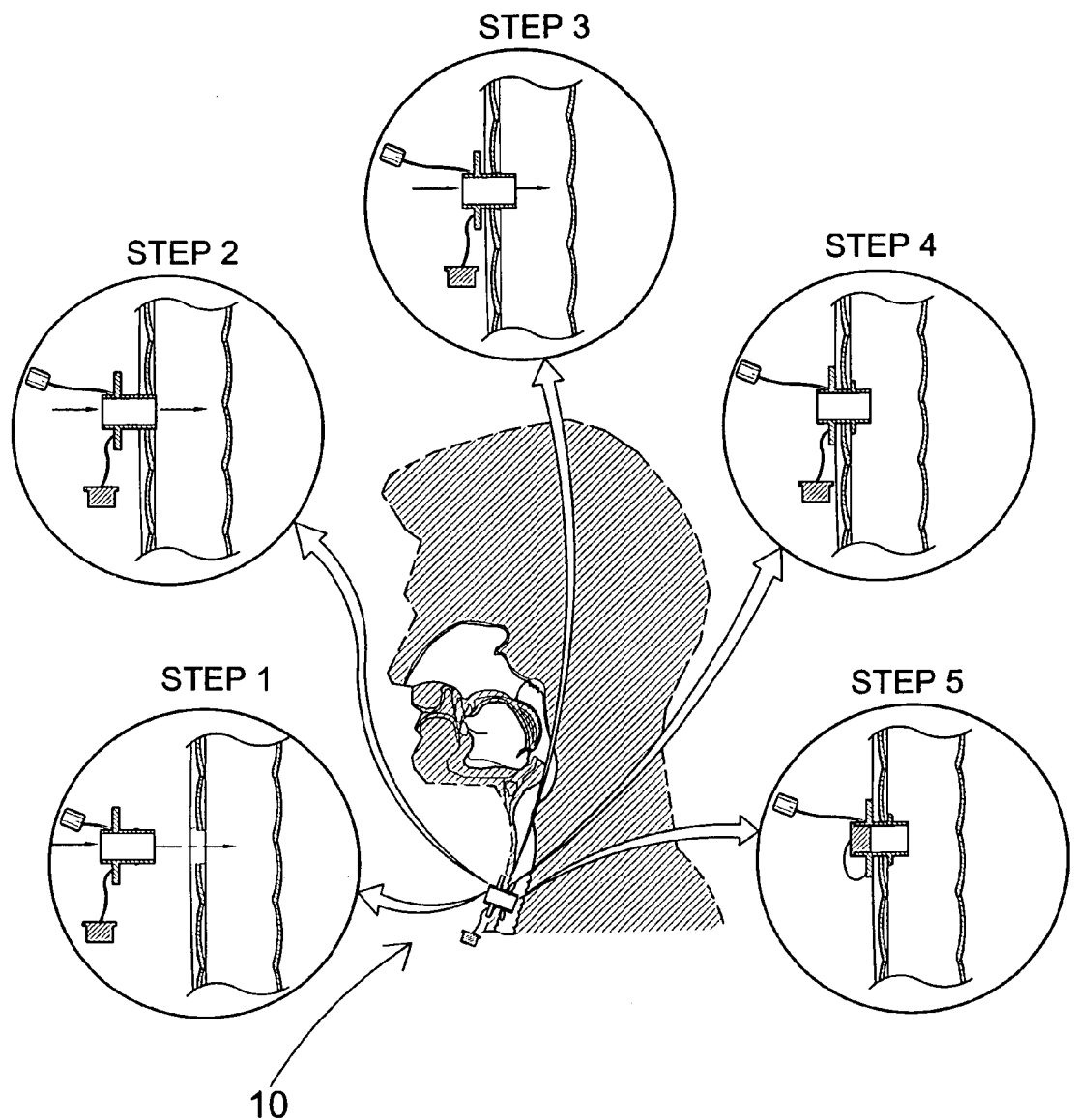
FIG. 1 is an illustrative view of the present invention as used.

With regard to reference numerals used, the following numbering is used throughout the drawings.

10 present invention
12 trachea tube
14 interior retaining member
16 outer flange
18 cap
20 trachea
22 arrows
24 opening to trachea
26 pilot balloon
28 annular space
30 conduit
32 air injection point
34 tether

DETAILED DESCRIPTION OF THE PREFERRED EMBODIMENT

The following discussion describes in detail one embodiment of the invention. This discussion should not be construed, however, as limiting the invention to those particular embodiments since practitioners skilled in the art will recognize numerous other embodiments as well. For a definition of the complete scope of the invention, the reader is directed to the appended claims.

Turning to FIG. 1, shown therein is an illustrative view of the present invention 10 as used. Shown is the present invention 10 comprising a trachea tube having an interiorly positioned retaining member and a flange forming an exteriorly positioned retaining member. The trachea tube has means for selectively sealing the tube. The tracheotomy tube of the present invention is provided with an inflatable element that permits the tube to be held firmly in the proper position upon inflation. The tube, when inserted into the trachea, is in frictional contact with the trachea to prevent significant air flow through the annular space between the tube and the trachea. Shown are steps 1 to 5 for using the present invention 10.

Figure 2:
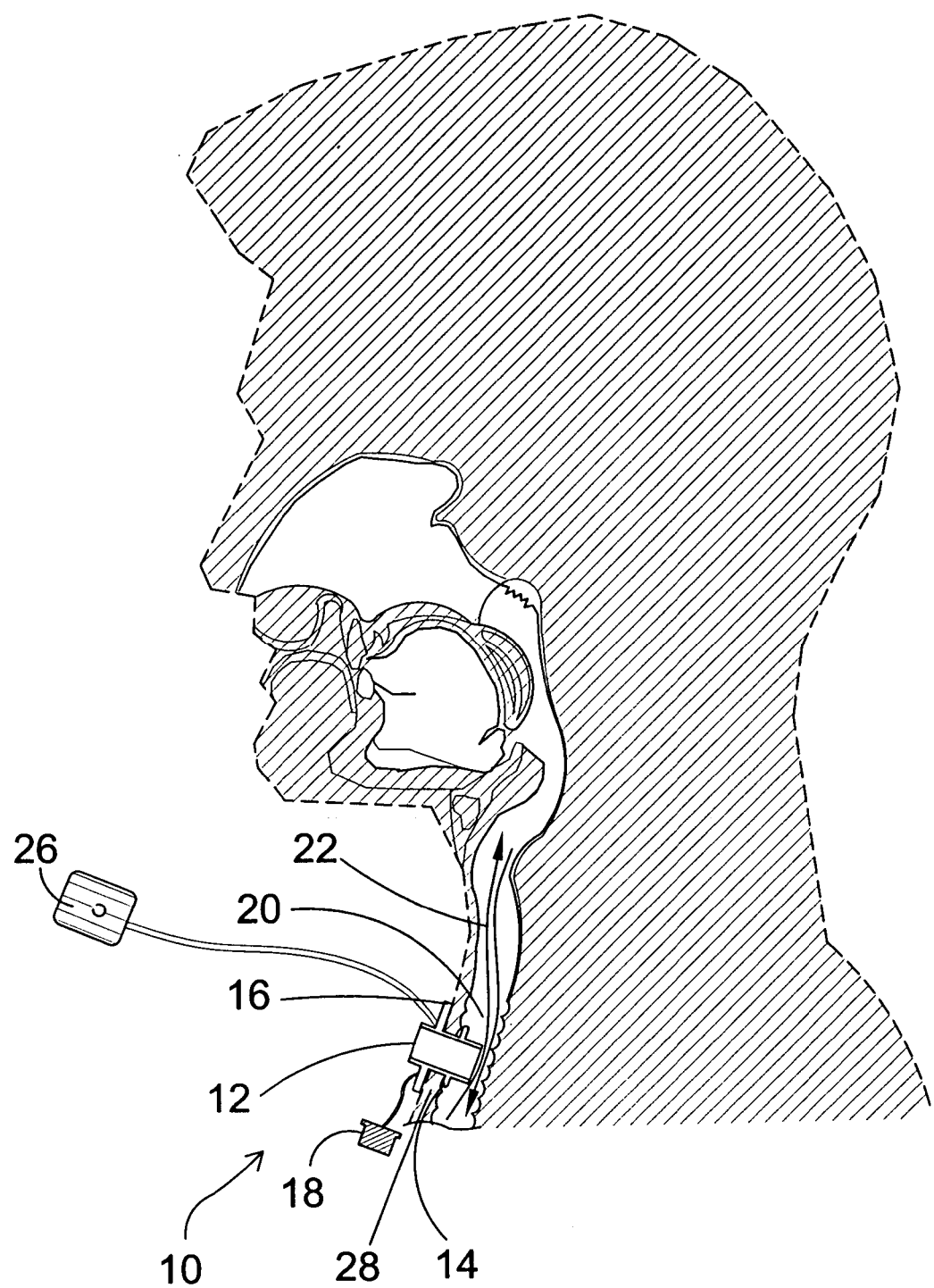
FIG. 2 is an illustrative view of the present invention as used.

Turning to FIG. 2, shown therein is an illustrative view of the present invention 10 as used. Shown is the present invention 10 comprising a trachea tube 12 having an interiorly positioned retaining member 14 in the form of a soft plastic inflatable balloon cuff and a flange 16 forming an exteriorly positioned retaining member forming an annular space therein between. The trachea tube 12 has means 18 such as a cap for selectively sealing the tube. The tracheotomy tube 12 of the present invention 10 is provided with an inflatable element 14 that permits the tube to be held firmly in the proper position upon inflation. The tube 12, when inserted into the trachea 20 is in frictional contact with the trachea to prevent significant air flow through the annular space 28 between the tube and the trachea opening. Also shown are arrows 22 showing the air flow and a pilot balloon 26.

Figure 3:
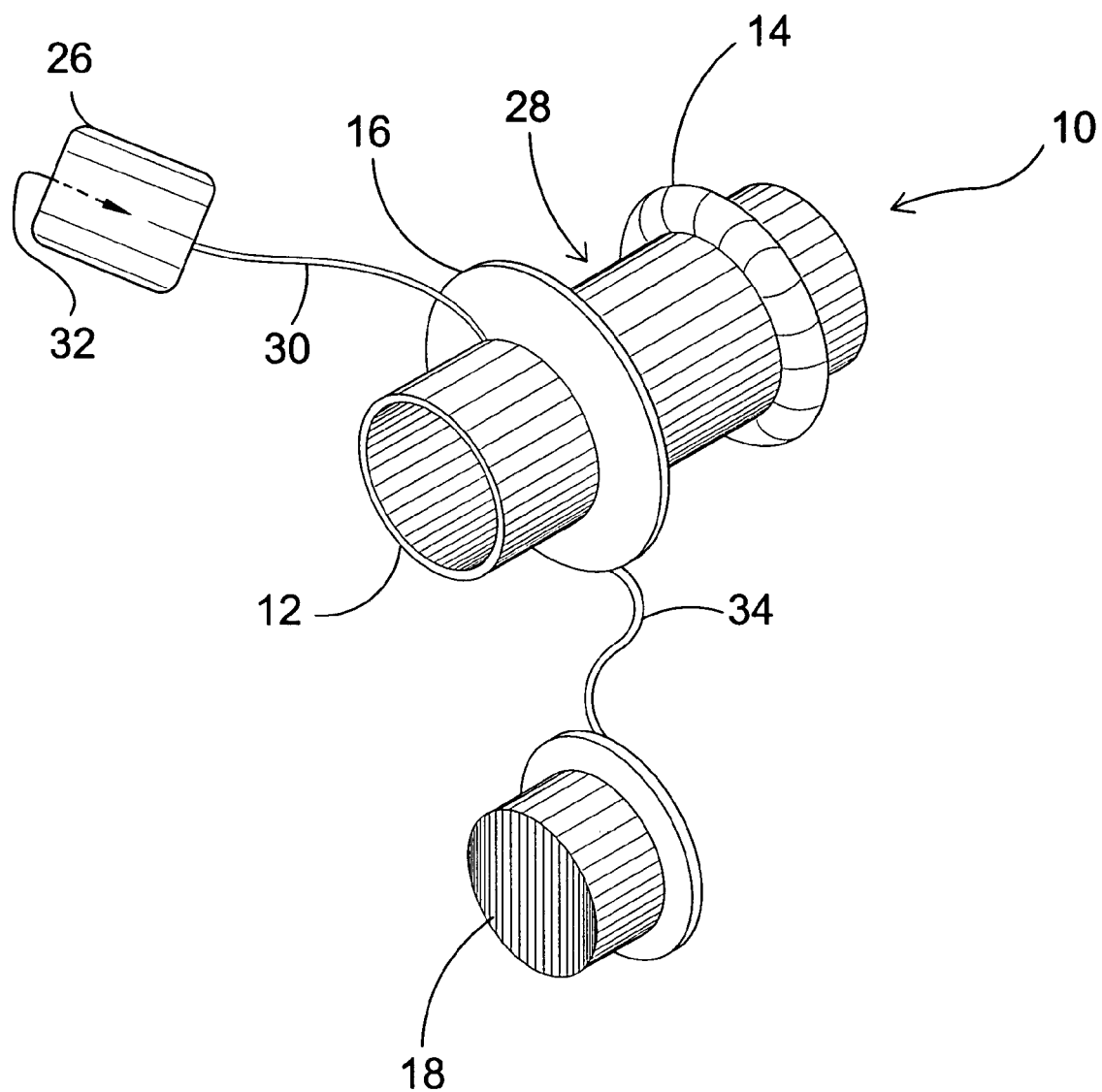
FIG. 3 is a perspective view of the present invention.

Turning to FIG. 3, shown therein is a perspective view of the present invention 10. Shown is the present invention 10 comprising a trachea tube 12 having an interiorly positioned retaining member 14 and a flange 16 forming an exteriorly positioned retaining member. The trachea tube 12 has means 18 on tether 34 for selectively sealing the tube. The tracheotomy tube 12 of the present invention 10 is provided with an inflatable element 14 that permits the tube to be held firmly in the proper position upon inflation. The tube 12, when inserted into the trachea, is in frictional contact with the trachea to prevent significant gas flow through the annular space 28 of the tube. Air is injected at 32 through a pilot hole using a syringe or the like (not shown) into the pilot balloon 26 which has an air conduit 30 which extends from the pilot balloon to the balloon cuff 14.

Figure 4:
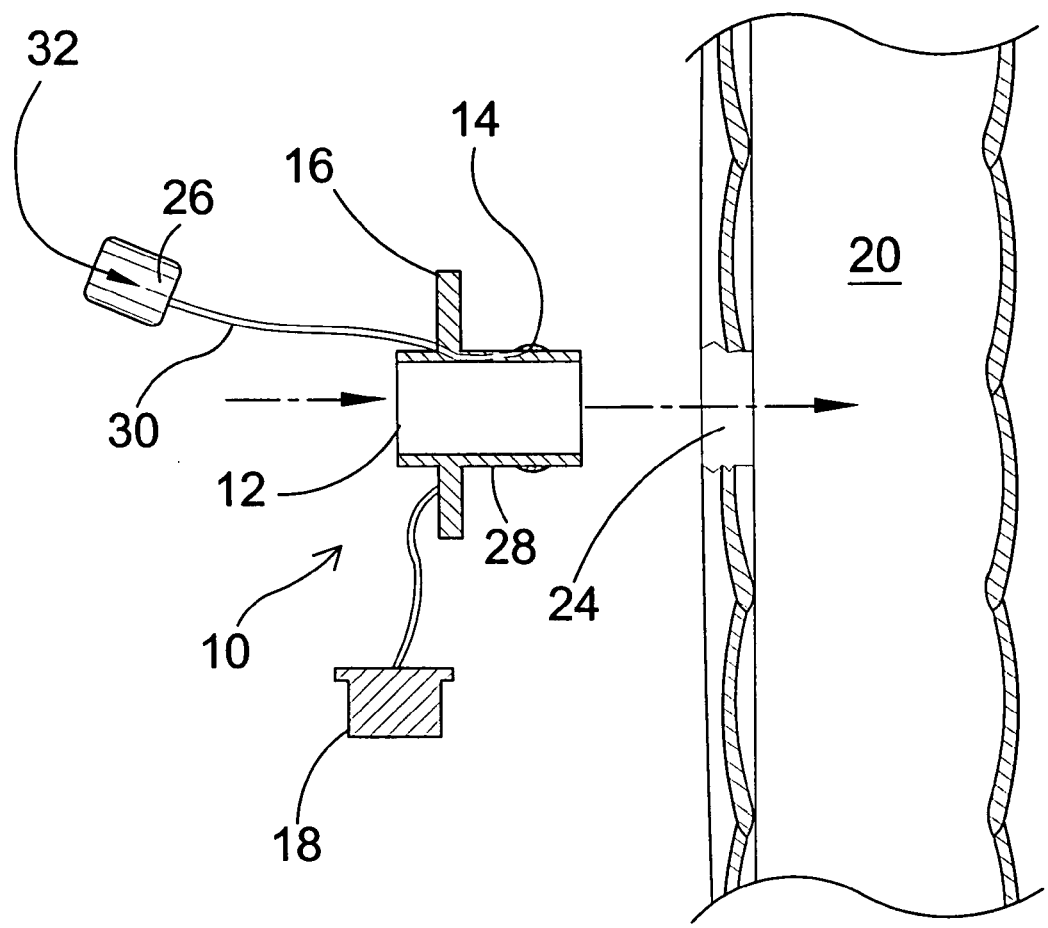
FIG. 4 is a sectional view of the present invention prior to insertion.

Turning to FIG. 4, shown therein is a sectional view of the present invention 10 prior to insertion. This is step 1 of the method of the present invention 10. Shown is the present invention 10 comprising a trachea tube 12 having an interiorly positioned retaining member 14 and a flange 16 forming an exteriorly positioned retaining member. The trachea tube 12 has means 18 for selectively sealing the tube. The tracheotomy tube 12 of the present invention 10 is provided with an inflatable element 14 that permits the tube to be held firmly in the proper position upon inflation. The tube 12, when inserted through the trachea opening 24 into the trachea 20, is in frictional contact with the trachea to prevent significant gas flow through the annular space 28 between the tube and the trachea opening 24. The present invention 10 allows for an open stoma, enhances speaking, allows clearance of secretion easier, suction, if needed, improves swallowing and allows the patient to be monitored. About three cc's (cubic centimeters) of air is injected at 32 into the pilot balloon 26 and through conduit 30.

Figure 5:
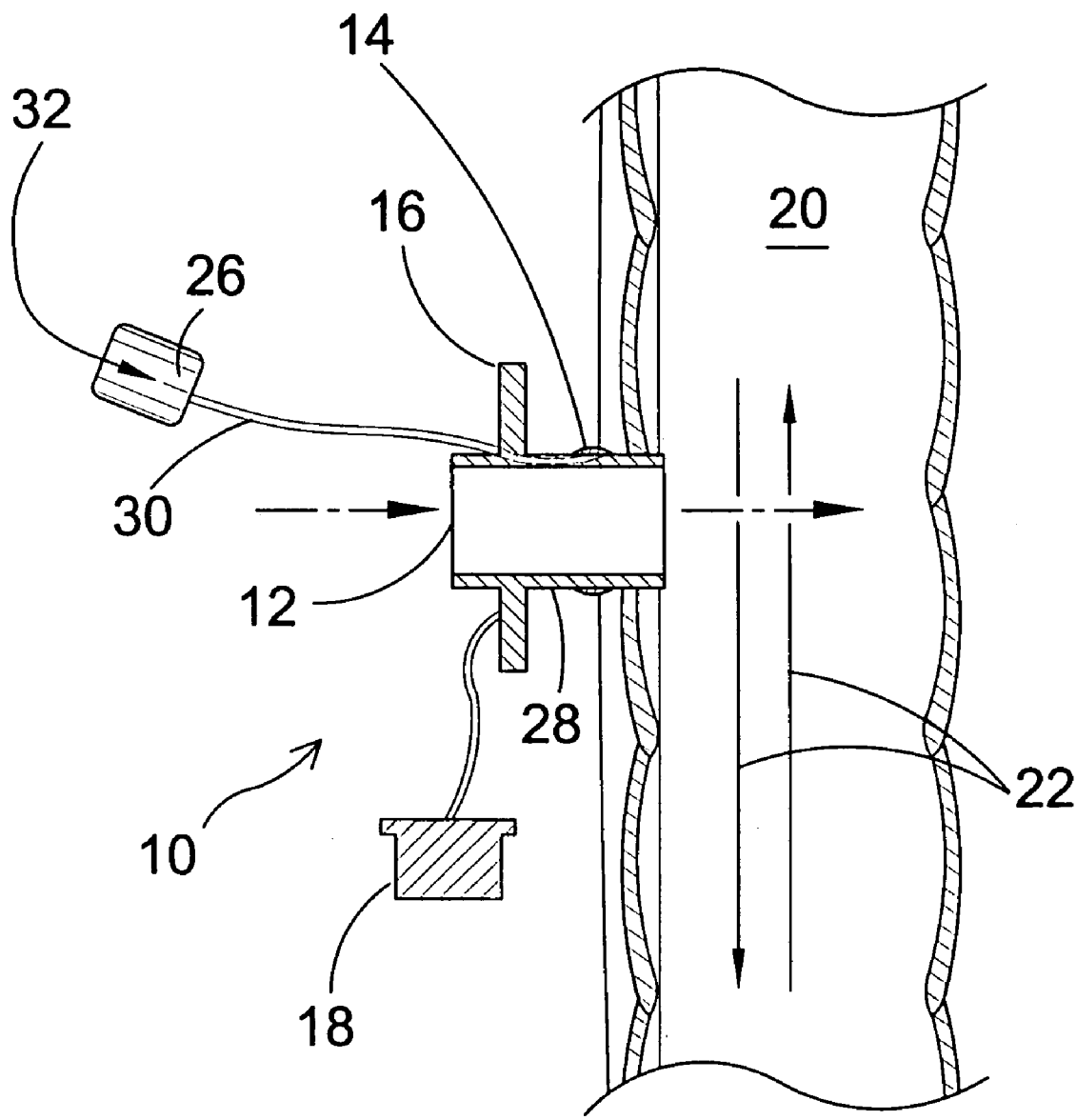
FIG. 5 is a sectional view of the present invention being inserted into the trachea.

Turning to FIG. 5, shown therein is a sectional view of the present invention 10 being inserted into the trachea 20. This is step 2 of the method of the present invention 10. Shown is the present invention 10 comprising a trachea tube 12 having an interiorly positioned retaining member 14 and a flange 16 forming an exteriorly positioned retaining member. The trachea tube 12 has means 18 for selectively sealing the tube. The tracheotomy tube 12 of the present invention 10 is provided with an inflatable element 14 that permits the tube 12 to be held firmly in the proper position upon inflation. The tube 12, when inserted into the trachea 20 is in frictional contact with the trachea to prevent significant gas flow through the annular space 28 of the tube. The present invention 10 allows for an open stoma, enhances speaking, allows clearance of secretion easier, suction if needed, improves swallowing and allows patient to be monitored. Arrows 22 show air movement. Three cc of air is injected at 32 into the pilot balloon 26 and through conduit 30.

Figure 6:
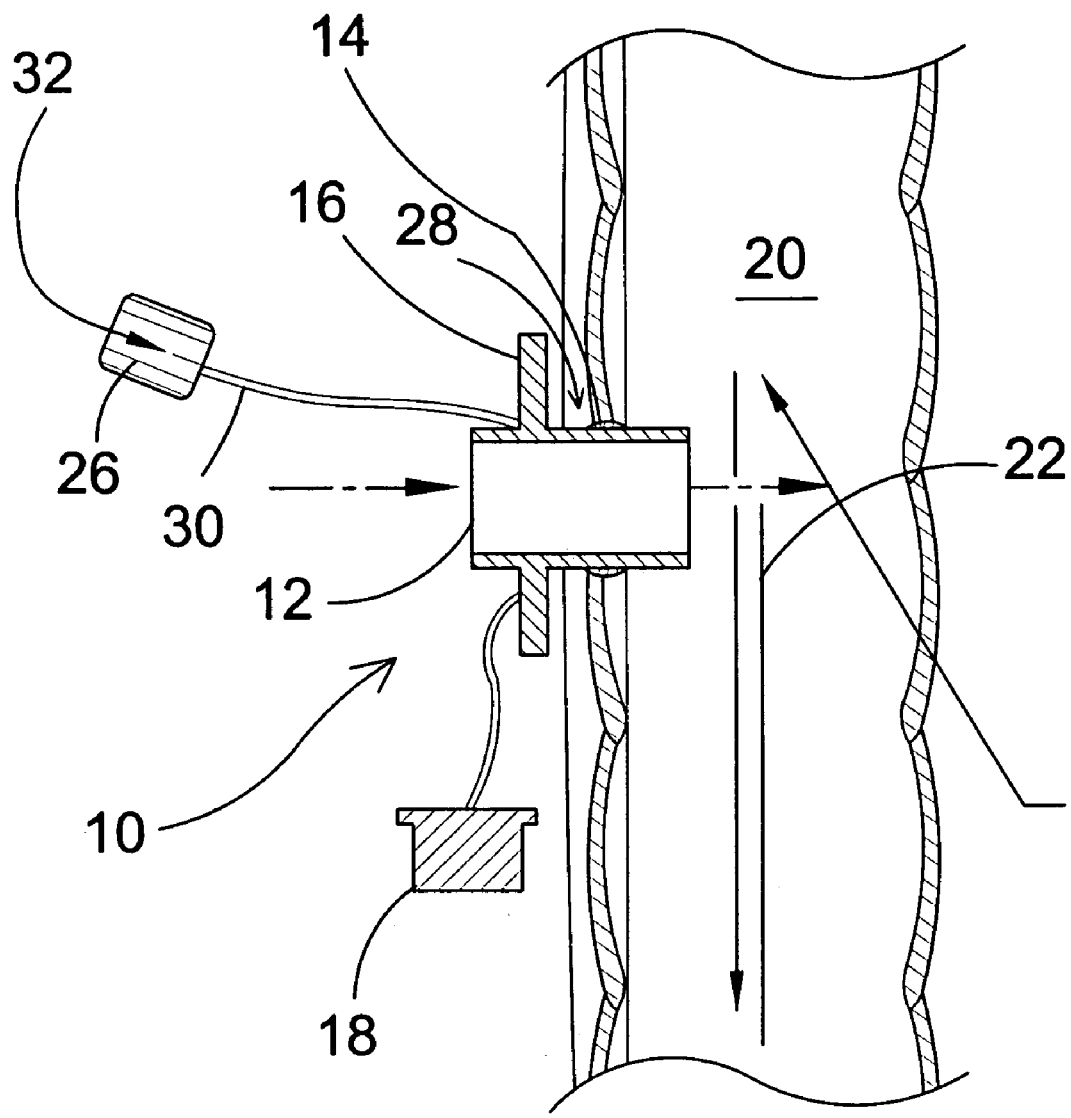
FIG. 6 is a sectional view of the present invention being inserted into the trachea.

Turning to FIG. 6, shown therein is a sectional view of the present invention 10 being inserted into the trachea 20. This is step 3 of the method of the present invention 10. Shown is the present invention 10 comprising a trachea tube 12 having an interiorly positioned retaining member 14 and a flange 16 forming an exteriorly positioned retaining member. The trachea tube 12 having means 18 for selectively sealing the tube. The tracheotomy tube 12 of the present invention 10 is provided with an inflatable element 14 that permits the tube to be held firmly in the proper position upon inflation. The tube 12, when inserted into the trachea 20 is in frictional contact with the trachea to prevent significant gas flow through the annular space 28 of the tube. The present invention 10 allows for an open stoma, enhances speaking, allows clearance of secretion easier, suction if needed, improves swallowing and allows patient to be monitored. Arrows 22 show air movement. Three cc of air is injected at 32 into the pilot balloon 26 and through conduit 30.

Figure 7:
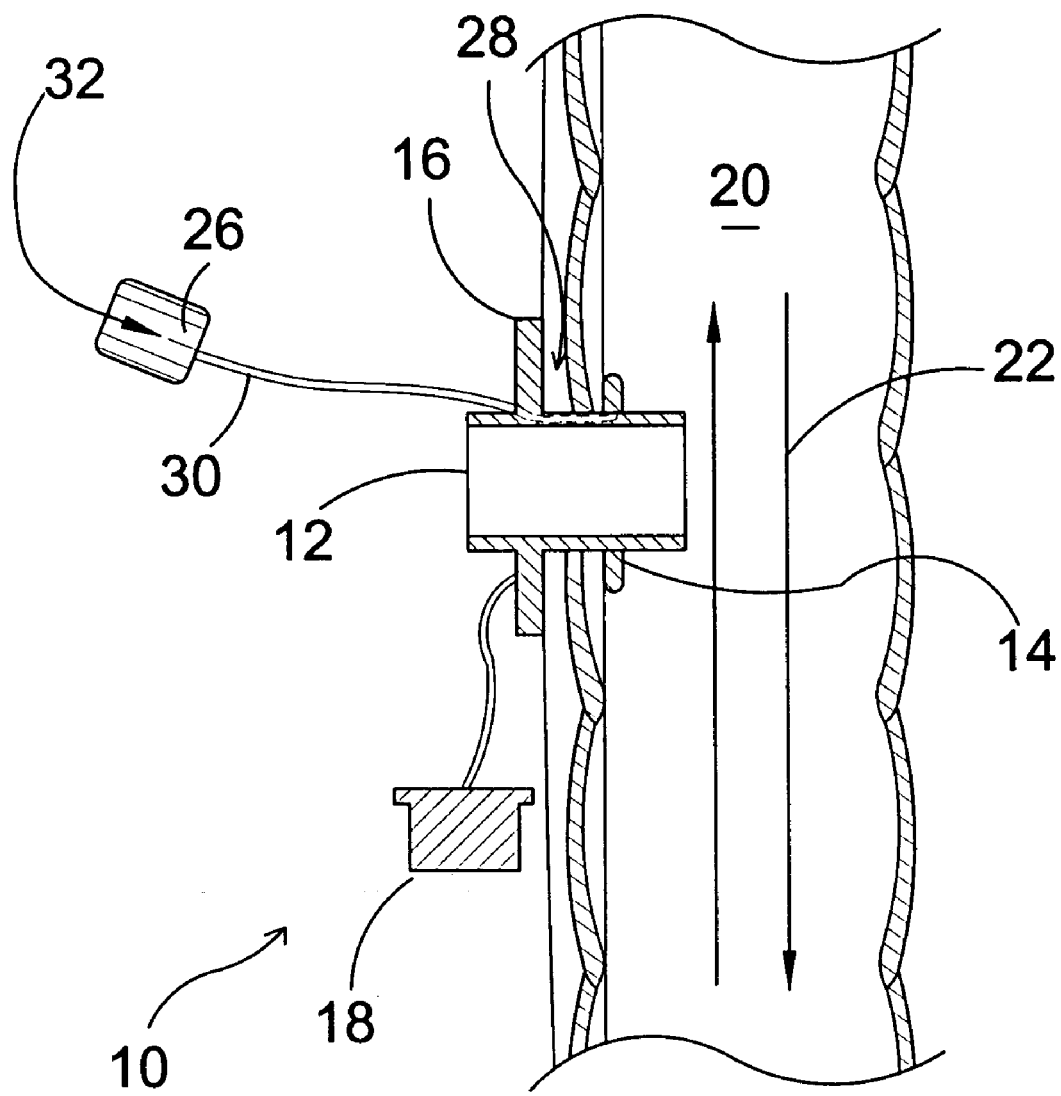
FIG. 7 is a sectional view of the present invention inserted into the trachea.

Turning to FIG. 7, shown therein is a sectional view of the present invention 10 inserted into the trachea 20. This is step 4 of the method of the present invention 10. Shown is the present invention 10 comprising a trachea tube 12 has an interiorly positioned retaining member 14 and a flange 16 forming an exteriorly positioned retaining member. The trachea tube 12 having means 18 for selectively sealing the tube. The tracheotomy tube 12 of the present invention 10 is provided with an inflatable element 14 that permits the tube to be held firmly in the proper position upon inflation. The tube 12, when inserted into the trachea 20 is in frictional contact with the trachea to prevent significant gas flow through the annular space 28 of the tube. The present invention 10 allows for an open stoma, enhances speaking, allows clearance of secretion easier, suction if needed, improves swallowing and allows patient to be monitored. Arrows 22 show air movement. Three cc of air is injected at 32 into the pilot balloon 26 and through conduit 30.

Figure 8:
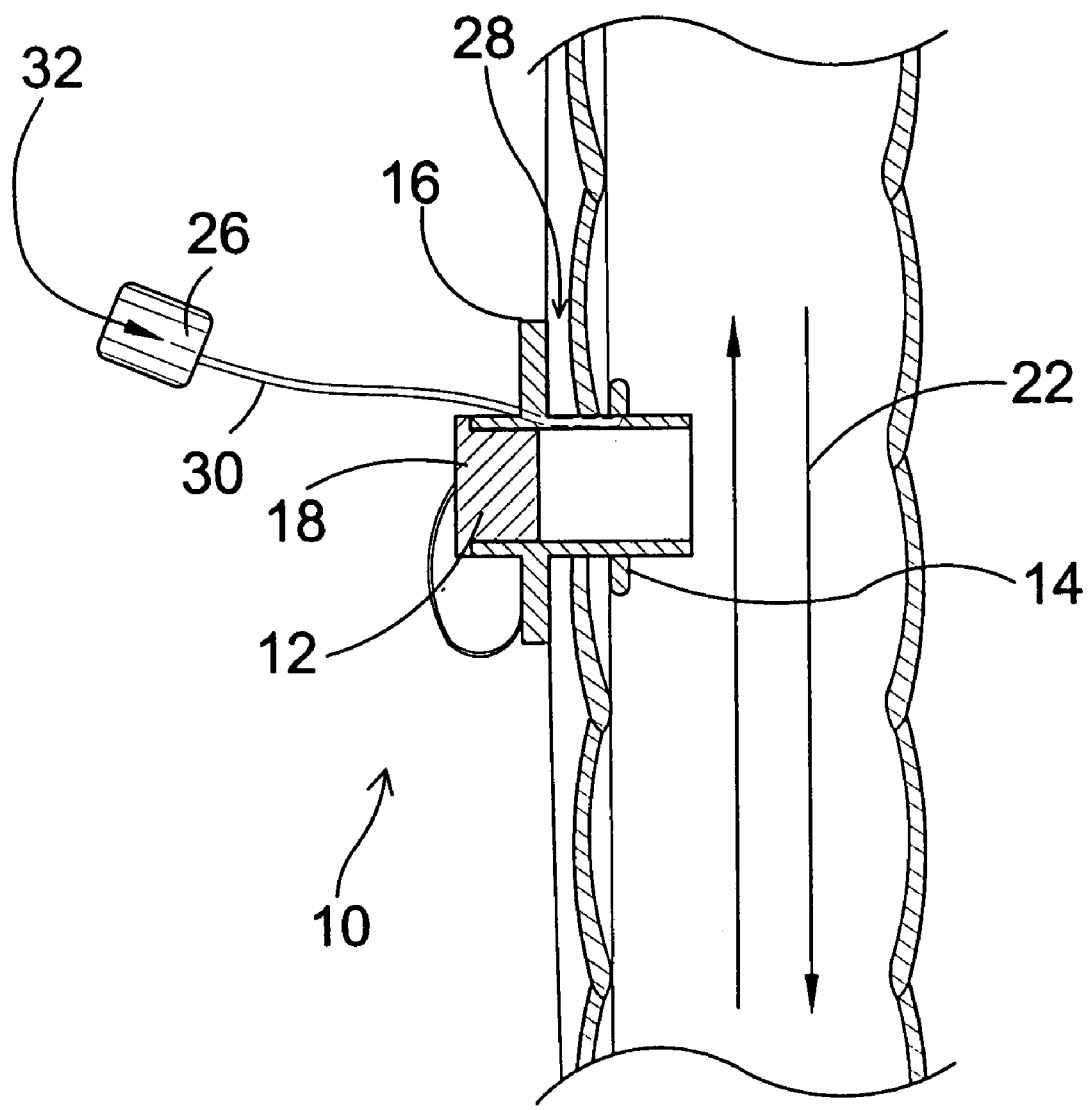
FIG. 8 is a sectional view of the present invention inserted into the trachea with cap inserted.

Turning to FIG. 8, shown therein is a sectional view of the present invention 10 inserted into the trachea 20 with cap 18 inserted. This is step 5 of the method of the present invention 10. Shown is the present invention 10 comprising a trachea tube 12 having an interiorly positioned retaining member 14 and a flange 16 forming an exteriorly positioned retaining member. The trachea tube 12 has means 18 for selectively sealing the tube. The tracheotomy tube 12 of the present invention 10 is provided with an inflatable element 14 that permits the tube to be held firmly in the proper position upon inflation. The tube 12, when inserted into the trachea 20 is in frictional contact with the trachea to prevent significant gas flow through the annular space 28 of the tube. The present invention 10 allows for an open stoma, enhances speaking, allows clearance of secretion easier, suction if needed, improves swallowing and allows patient to be monitored. Arrows 22 show air flow. Three cc of air is injected at 32 into the pilot balloon 26 and through conduit 30.

I claim:

1. A trachea tube for insertion into the trachea of a user, consisting of:

a) a straight tube having first and second opposing ends, wherein said first end is adapted to be inserted into the trachea of the user to permit air to pass therethrough, said tube having a wall the length of said tube being such as to extend only part way into a trachea for allowing air flow through said trachea past said tube;

b) an annular flange being disposed between said first and second ends of said tube, wherein said annular flange retains said second end of said tube on the exterior of the trachea of the user by preventing said tube from filling into the interior of the trachea;

c) an annular balloon cuff being disposed between said annular flange and said first end of said tube; and, d) wherein said annular balloon cuff is inflatable so as to secure said tube to the trachea, wherein said annular balloon cuff has a first configuration of being uninflated and a second configuration of being inflated, wherein said trachea is secured between said inflated annular balloon cuff and said annular flange.

2. The trachea tube of claim 1, further comprising a pilot balloon, a first end of an air conduit being connected to said pilot balloon and a second end adapted for connection to said annular balloon cuff to permit the annular balloon cuff to be inflated.

3. The trachea tube of claim 2, wherein a portion of said air conduit is disposed in said wall of said tube.

4. The trachea tube of claim 3, further comprising a cap adapted for placement on said second end of said tube so as to seal the tube after placement in the trachea.

5. The trachea tube of claim 4, further comprising a tether for connecting said cap to said tube.

6. The trachea tube of claim 5, wherein said annular balloon cuff has an inflated volume of about three cubic centimeters to permit the annular balloon cuff to be inflated with about three cubic centimeters of air supplied by a syringe, and be of substantially uniform size and shape surrounding said tube.

7. The trachea tube of claim 6, further comprising an annular space being disposed around said tube between said annular flange and said annular balloon cuff, wherein said annular space forms a substantially air tight seal between said tube, said trachea, said annular flange and said inflated annular balloon cuff.

8. A method for a trachea tube for insertion into the trachea of a user, comprising the steps of
   a) providing an opening into the trachea of a user;
   b) forming a straight tube having first and second opposing ends and then inserting the first end of the tube into the trachea of the user to permit air to pass therethrough, said tube extending only part way through the trachea to allow flow of air in said trachea past said tube;
   c) forming an annular flange on the tube between the first and second ends of the tube so that the annular flange can retain the second end of the tube on the exterior of the trachea of the user by preventing the tube from ing into the interior of the trachea;
   d) forming an annular balloon cuff on the tube between the annular flange and the first end of the tube so that the annular balloon cuff has a first configuration of being uninflated and a second configuration of being inflated, wherein the annular balloon cuff is uninflated when the tube is ins into the trachea; and,
   e) inflating the annular balloon cuff so as to secure the tube to the trachea by securing the opening of the trachea between the inflated annular balloon cuff and the annular flange.

9. The method of claim 8, farther comprising the steps of providing a pilot balloon and connecting a first end of an air conduit to the pilot balloon and connecting a second end of the air conduit to the annular balloon cuff to permit the annular balloon cuff to be inflated by forcing air through the air conduit.

10. The method of claim 9, further comprising the step of forming a portion of the air conduit is formed in the wall of the tube.

11. The method of claim 10, further comprising the step of providing a cap for placement on the second end of the tube so as to seal the tube after placement in the trachea.

12. The method of claim 11, further comprising the step of attaching a cap to the tube using a tether.

13. The method of claim 12, further comprising the step of sizing and shaping the annular balloon cuff to have an inflated volume of about three cubic centimeters to permit the annular balloon cuff to be inflated with about three cubic centimeters of air supplied by a syringe and forming a uniformly shaped and sized cuff around said tube.

14. The method of claim 13, further comprising the step of inflating the annular balloon cuff so that an annular space is formed on the tube between the annular flange and the inflated annular balloon cuff so that the annular space forms a substantially air tight seal between the tube, the trachea, the annular flange and the inflated annular balloon cuff.

* * * * *